United States Patent [19]

Saghai-Maroof et al.

[11] Patent Number: 5,574,210

[45] Date of Patent: Nov. 12, 1996

[54] GRAY LEAF SPOT RESISTANT CORN AND THE PRODUCTION THEREOF

[75] Inventors: Mohammad Saghai-Maroof, Blacksburg, Va.; George K. Rufener, II, Johnston, Iowa; Erik Stromberg, Blacksburg, Va.; Ronald P. Mowers; Albert J. Balducchi, both of Ames, Iowa

[73] Assignee: Zeneca Limited, London, England

[21] Appl. No.: 466,098

[22] Filed: Jun. 6, 1995

[51] Int. Cl.$^6$ .......................... A01H 5/00; A01H 1/100; C12N 5/04; C12N 15/00
[52] U.S. Cl. ............. 800/200; 800/250; 800/DIG. 56; 47/58; 47/DIG. 1; 435/172.1; 435/172.3
[58] Field of Search ........................... 800/200, 205, 800/250, DIG. 56; 47/58; 435/172.3, 172.1

[56] References Cited

U.S. PATENT DOCUMENTS 5,385,835  1/1995  George et al. .

FOREIGN PATENT DOCUMENTS

WO84/04758  12/1984  WIPO .
WO89/07647  8/1989  WIPO .

OTHER PUBLICATIONS

Bubeck, D. M., Goodman, M. M., Beavis, W. D., and Grant, D. Cell Biology and Molecular Genetics—Quantitative Trait Loci Controlling Resistance to Gray Leaf Spot in Maize. Published in *Crop Science* 33:838–847 (1993).

*Primary Examiner*—Gary Benzion
*Attorney, Agent, or Firm*—Dana Rewoldt

[57] ABSTRACT

This invention relates to maize plants and a method of producing same, which are resistant to Gray Leaf Spot which will hereinafter simply be referred to as GLS. More particularly this invention relates to the introgression in maize of identifiable genetic material capable of causing the plant to be resistant to GLS. Additionally, the present invention relates to the introgression of desired genetic material from one or more parent plants into progeny plants with precision and accuracy.

12 Claims, 15 Drawing Sheets

FIG. 2

LOCATION ANALYSIS

| HYBRID | YLD | MST | %SL | %RL | %DE | TWT | R | L |
|---|---|---|---|---|---|---|---|---|
| HYBRID Z 85321T | 176 | 23.7 | 0 | 2.1 | 0 | 51.5 | 4 | 2 |
| HYBRID A | 184 | 24.8 | 0.4 | 0 | 0 | 50 | 4 | 2 |
| HYBRID B | 186 | 26.2 | 0 | 0 | 0 | 50.5 | 4 | 2 |

YLD — YIELD
MST — MOISTURE
%SL — PERCENT STALK LODGE
%RL — PERCENT ROOT LODGE
%DE — DROPPED EAR
TWT — TEST WEIGHT
R — REPETITIONS
L — LOCATION

CHROMOSOME 1-A

FIG. 3A-2

CHROMOSOME 1-B

Break Line

```
163 ──┬── php20855      bnl(nia4) npi224g
      │                 ncr(nra)
1.09  │                 npi605
      │                 npi566
      │                 umc23a umc33
182 ──┼── /umc128/      npi236 bnl17.15(bt2)
183 ──┼── mdh4          rny(pcr1) umc128 npi447
185 ──┼── umc83         umc37 bnl17.06 mdh4
190 ──┼── umc181(bz2)   npi569 npi573 umc83
192 ──┼── umc316        npi120 npi255 ucsd61e
                        bz2
1.10                    bnl8.10
203 ──┼── umc184a(glb1) tbp1
205 ──┼── /umc140/      ynh20
                        bnl15.18 bnl17.04
213 ──┼── umc197(b32)   umc107a
214 ──┼── rpa6b         phya1 bnl17.21
216 ──┼── umc107a       umc106a
1.11
223 ──┼── adh1          adh1
      │   /npi225/
                        npi98a pge(c2) umc72b
                        npi407 bnl17.18b npi581a
1.12                    umc147b bnl7.25
238 ──┼── phi1          phi1 pge5b
      │   rpa7a
240 ──┼── umc161        npi226b 247 ──┼── /npi238/      bnl8.08a
1.13                    npi238
                        gdh1

258 ──┼── /bnl8.29a/    bnl8.29a ucsd44a npi241a 1.14

282 ──┼── /umc84/       umc84 csh(chi1)

1.15

300 ──┼── /bnl6.32/     bnl6.32 npi361I
1.16
                        acp4
313 ──┼── acp4
                        fd3
```

CHROMOSOME 2-A

CHROMOSOME 5-B

FIG. 4

GRAY LEAF SPOT RESISTANCE
BE70 VA14 F2-F3 POPULATION

| CHR # | PR>F | R-SQUARE | FALC A | EST EFFECT | GENE ACTION | DONOR PARENT | FLANKING PROBES | PROBE DIST.* |
|---|---|---|---|---|---|---|---|---|
| 1 | 0.001 | 0.62 | 0.67 | 1.35 | ADDIT | VA14 | U67-B559 | 6.9 |
| 2 | 0.001 | 0.06 | 0.22 | 0.44 | ADDIT | VA14 | U34-U131 | 13 |
| 3 | 0.03 | 0.05 | 0.23 | 0.46 | DOMIN | BE70 | U46B-N446 | 9.9 |
| 4 | 0.001 | 0.15 | 0.33 | 0.67 | ADDIT | BE70 | N444-U15 | 3.4 |
| 5 | 0.001 | 0.06 | 0.21 | 0.43 | RECESS | VA14 | B436-B571 | 8.8 |
| 7 | 0.01 | 0.07 | 0.25 | 0.5 | RECESS | BE70 | N433-B1606 | 9 |
| 8 | 0.001 | 0.14 | 0.27 | 0.55 | RECESS | VA14 | U30-N268 | 28 |

CHROMOSOMAL REGIONS WITH MAJOR GLS EFFECTS FROM VA14

* DISTANCE IN cM BETWEEN PROBES CAPPING THE CHROMOSOMAL REGIONS.

FIG. 5A

| CHROM | MAP # | GLSF2 | | | | | GLSF3 | | | | |
|---|---|---|---|---|---|---|---|---|---|---|---|
| | | SIG | PR>F | RSQ | FALC A | PR>T | SIG | PR>F | RSQ | FALC A | PR>T |
| 1 | B0562A | 0 | 0.00 | 0.08 | -0.42 | 0.00 | 1 | 0.00 | 0.06 | -0.16 | 0.01 |
| 1 | N0209 B | 0 | 0.00 | 0.14 | -0.58 | 0.00 | 0 | 0.00 | 0.09 | -0.28 | 0.00 |
| 1 | N0234 B | 0 | 0.00 | 0.18 | -0.65 | 0.00 | 0 | 0.00 | 0.14 | -0.34 | 0.00 |
| 1 | U0011 B | 0 | 0.00 | 0.20 | -0.67 | 0.00 | 0 | 0.00 | 0.17 | -0.38 | 0.00 |
| 1 | U0013 B | 0 | 0.00 | 0.27 | -0.79 | 0.00 | 0 | 0.00 | 0.23 | -0.43 | 0.00 |
| 1 | UU067 B | 0 | 0.00 | 0.45 | -1.02 | 0.00 | 0 | 0.00 | 0.51 | -0.64 | 0.00 |
| 1 | B0559 B | 0 | 0.00 | 0.50 | -1.02 | 0.00 | 0 | 0.00 | 0.62 | -0.67 | 0.00 |
| 1 | U0058 B | 0 | 0.00 | 0.44 | -1.00 | 0.00 | 0 | 0.00 | 0.55 | -0.66 | 0.00 |
| 1 | U0023 B | 0 | 0.00 | 0.29 | -0.86 | 0.00 | 0 | 0.00 | 0.30 | -0.52 | 0.00 |
| 1 | U0033 B | 0 | 0.00 | 0.30 | -0.88 | 0.00 | 0 | 0.00 | 0.32 | -0.54 | 0.00 |
| 1 | N0447 D | 0 | 0.00 | 0.17 | -0.65 | 0.00 | 0 | 0.00 | 0.19 | -0.40 | 0.00 |
| 1 | U0037 B | 0 | 0.00 | 0.17 | -0.64 | 0.00 | 0 | 0.00 | 0.20 | -0.43 | 0.00 |
| 1 | U0083 B | 0 | 0.00 | 0.15 | -0.58 | 0.00 | 0 | 0.00 | 0.14 | -0.36 | 0.00 |
| 1 | N0120 D | 0 | 0.00 | 0.15 | -0.58 | 0.00 | 0 | 0.00 | 0.16 | -0.36 | 0.00 |
| 2 | N0269 | | 0.17 | 0.02 | -0.24 | 0.08 | 5 | 0.02 | 0.06 | -0.18 | 0.03 |
| 2 | U0034 B | 5 | 0.01 | 0.04 | -0.33 | 0.00 | 1 | 0.00 | 0.06 | -0.22 | 0.00 |
| 2 | U0131 D | | 0.54 | 0.01 | -0.12 | 0.29 | | 0.21 | 0.02 | -0.12 | 0.10 |
| 2 | N0297 D | | 0.46 | 0.01 | -0.08 | 0.60 | | 0.82 | 0.00 | -0.06 | 0.53 |
| 2 | U0139 B | | 0.51 | 0.01 | -0.05 | 0.64 | | 0.66 | 0.00 | -0.01 | 0.84 |
| 2 | U0055GB | 5 | 0.03 | 0.05 | -0.29 | 0.05 | | 0.22 | 0.02 | -0.15 | 0.12 |

FIG. 5B

| CHROM | MAP # | GLSF2 ||||| GLSF3 |||||
|---|---|---|---|---|---|---|---|---|---|---|---|
| | | SIG | PR>F | RSQ | FALC A | PR>T | SIG | PR>F | RSQ | FALC A | PR>T |
| 2 | U0022 B | | 0.84 | 0.00 | -0.01 | 0.96 | | 0.17 | 0.03 | 0.12 | 0.18 |
| 2 | U0004 B | | 0.97 | 0.00 | -0.02 | 0.91 | | 0.20 | 0.02 | 0.14 | 0.13 |
| 3 | B0815 B | | 0.94 | 0.00 | -0.05 | 0.74 | | 0.71 | 0.01 | 0.07 | 0.45 |
| 3 | U0046 B | | 0.58 | 0.01 | 0.16 | 0.31 | | 0.75 | 0.00 | 0.07 | 0.46 |
| 3 | N0446 B | | 0.22 | 0.02 | 0.25 | 0.10 | 5 | 0.03 | 0.05 | 0.23 | 0.02 |
| 3 | N0296 B | | 0.26 | 0.02 | -0.22 | 0.14 | | 0.36 | 0.02 | -0.10 | 0.26 |
| 3 | U0016 B | | 0.07 | 0.02 | -0.23 | 0.05 | | 0.12 | 0.02 | -0.15 | 0.04 |
| 3 | U0086 B | | 0.78 | 0.00 | -0.08 | 0.62 | | 0.79 | 0.00 | -0.06 | 0.54 |
| 3 | N0457 B | | 0.99 | 0.00 | 0.01 | 0.97 | | 0.79 | 0.00 | -0.07 | 0.50 |
| 4 | U0087 D | | 0.10 | 0.00 | 0.21 | 0.06 | | 0.28 | 0.01 | 0.10 | 0.16 |
| 4 | N0396 D | | 0.70 | 0.01 | 0.04 | 0.83 | | 0.92 | 0.00 | -0.03 | 0.80 |
| 4 | U0066 B | | 0.10 | 0.03 | 0.24 | 0.09 | | 0.28 | 0.02 | 0.13 | 0.16 |
| 4 | U0019 B | 1 | 0.00 | 0.05 | 0.23 | 0.04 | 1 | 0.01 | 0.05 | 0.18 | 0.01 |
| 4 | N0444 B | 0 | 0.00 | 0.17 | 0.54 | 0.00 | 0 | 0.00 | 0.15 | 0.33 | 0.00 |
| 4 | U0015 B | 0 | 0.00 | 0.17 | 0.55 | 0.00 | 0 | 0.00 | 0.15 | 0.32 | 0.00 |
| 4 | N0451 B | | 0.69 | 0.01 | 0.07 | 0.60 | | 0.64 | 0.01 | 0.06 | 0.51 |
| 5 | N0268 B | | 0.75 | 0.00 | -0.02 | 0.90 | | 0.88 | 0.00 | -0.03 | 0.73 |
| 5 | N0409 B | | 0.70 | 0.00 | -0.10 | 0.50 | | 0.69 | 0.01 | -0.08 | 0.39 |
| 5 | B0502 B | | 0.14 | 0.02 | -0.18 | 0.07 | 1 | 0.01 | 0.05 | -0.19 | 0.00 |
| 5 | U0001 B | | 0.19 | 0.01 | -0.18 | 0.08 | 5 | 0.03 | 0.03 | -0.16 | 0.01 |

FIG. 5C

| CHROM | MAP # | GLSF2 | | | | | GLSF3 | | | | |
|---|---|---|---|---|---|---|---|---|---|---|---|
| | | SIG | PR>F | RSQ | FALC A | PR>T | SIG | PR>F | RSQ | FALC A | PR>T |
| 5 | B0436 B | | 0.17 | 0.02 | -0.19 | 0.06 | 1 | 0.01 | 0.05 | -0.19 | 0.00 |
| 5 | B0571 B | | 0.06 | 0.02 | -0.24 | 0.02 | 1 | 0.00 | 0.06 | -0.21 | 0.00 |
| 5 | U0054 A | 5 | 0.62 | 0.01 | 0.05 | 0.74 | | 0.53 | 0.02 | -0.06 | 0.55 |
| 5 | U0051 D | | 0.75 | 0.01 | 0.01 | 0.95 | | 0.62 | 0.01 | -0.07 | 0.46 |
| 6 | U0085 D | | 0.06 | 0.02 | 0.05 | 0.71 | | 0.86 | 0.00 | -0.04 | 0.64 |
| 6 | N0373 B | 5 | 0.02 | 0.05 | -0.08 | 0.59 | | 0.23 | 0.02 | -0.06 | 0.50 |
| 6 | N0223 B | | 0.19 | 0.02 | 0.16 | 0.27 | | 0.22 | 0.02 | 0.12 | 0.17 |
| 6 | U0021 B | | 0.95 | 0.00 | 0.04 | 0.76 | | 0.69 | 0.01 | 0.05 | 0.58 |
| 6 | N0252 B | | 0.54 | 0.01 | 0.02 | 0.88 | | 0.07 | 0.04 | 0.06 | 0.53 |
| 6 | N0280 B | | 0.09 | 0.03 | 0.23 | 0.15 | | 0.19 | 0.03 | 0.05 | 0.60 |
| 7 | U0045 B | | 0.92 | 0.00 | 0.03 | 0.78 | | 0.86 | 0.00 | 0.03 | 0.69 |
| 7 | B0606 B | | 0.15 | 0.02 | 0.18 | 0.09 | | 0.07 | 0.03 | 0.15 | 0.03 |
| 7 | N0433 B | 5 | 0.02 | 0.05 | 0.27 | 0.05 | 1 | 0.01 | 0.07 | 0.25 | 0.00 |
| 7 | U0116 D | 5 | 0.03 | 0.03 | 0.20 | 0.05 | | 0.54 | 0.01 | 0.04 | 0.59 |
| 8 | N0114 B | | 0.62 | 0.01 | 0.13 | 0.39 | | 0.50 | 0.01 | 0.10 | 0.26 |
| 8 | B0911 B | | 0.34 | 0.01 | -0.18 | 0.22 | | 0.32 | 0.02 | -0.01 | 0.92 |
| 8 | N0110 D | | 0.52 | 0.01 | -0.16 | 0.26 | | 0.99 | 0.00 | 0.02 | 0.87 |
| 8 | U0120 B | | 0.64 | 0.01 | -0.14 | 0.35 | | 0.76 | 0.01 | -0.06 | 0.50 |
| 8 | U0048 B | 0 | 0.00 | 0.11 | -0.41 | 0.00 | 0 | 0.00 | 0.10 | -0.26 | 0.00 |
| 8 | U0030 | 0 | 0.00 | 0.11 | -0.39 | 0.00 | 0 | 0.00 | 0.14 | -0.27 | 0.00 |

FIG. 5D

| CHROM | MAP # | | GLSF2 | | | | | GLSF3 | | | |
|---|---|---|---|---|---|---|---|---|---|---|---|
| | | SIG | PR>F | RSQ | FALC A | PR>T | SIG | PR>F | RSQ | FALC A | PR>T |
| 8 | N0107 D | 1 | 0.01 | 0.04 | -0.16 | 0.14 | | 0.09 | 0.02 | -0.08 | 0.23 |
| 9 | COBZ1 A | | 0.09 | 0.03 | -0.19 | 0.19 | | 0.26 | 0.02 | -0.11 | 0.25 |
| 9 | U0055 B | | 0.36 | 0.01 | -0.21 | 0.16 | | 0.14 | 0.03 | -0.13 | 0.16 |
| 9 | U0095 B | | 0.86 | 0.00 | 0.01 | 0.94 | | 0.07 | 0.04 | -0.21 | 0.03 |
| 9 | N0427 B | | 0.53 | 0.01 | 0.04 | 0.81 | | 0.14 | 0.03 | -0.17 | 0.09 |
| 9 | B0509 B | | 0.75 | 0.00 | -0.10 | 0.50 | | 0.46 | 0.01 | -0.11 | 0.25 |
| 10 | B0304 B | | 0.71 | 0.00 | 0.13 | 0.42 | | 0.95 | 0.00 | 0.03 | 0.77 |
| 10 | N0288 B | | 0.98 | 0.00 | 0.02 | 0.89 | | 0.56 | 0.01 | -0.09 | 0.34 |
| 10 | N0445 A | | 0.65 | 0.01 | -0.11 | 0.44 | | 0.19 | 0.03 | -0.14 | 0.09 |
| 10 | N0264 B | | 0.89 | 0.00 | -0.06 | 0.72 | | 0.23 | 0.02 | -0.16 | 0.10 |
| 10 | U0044 B | | 0.79 | 0.00 | 0.08 | 0.59 | | 0.96 | 0.00 | -0.01 | 0.94 |

GRAY LEAF SPOT RESISTANT CORN AND THE PRODUCTION THEREOF

FIELD OF THE INVENTION

This invention relates to maize plants and a method of producing same, which are resistant to Gray Leaf Spot which will hereinafter simply be referred to as GLS. More particularly this invention relates to the introgression in maize of identifiable genetic material capable of causing the plant to be resistant to GLS. Additionally, the present invention relates to the introgression of desired genetic material from one or more parent plants into progeny plants with precision and accuracy.

BACKGROUND OF THE INVENTION

Historically, maize (corn) has been used as a source of food for human and animal consumption. Today, maize supplies about twenty percent of the world's calories. Any environmental stress factor that affects maize can have an impact on maize availability. Thus reduction of the sensitivity of maize to GLS is understandably of importance. Gray leaf spot can result in yield loss as great as 20%.

Gray leaf spot has gained prominence the last decade. It has the potential to become a significant problem, not only in the mid-Atlantic region of the U.S. but in other major corn producing areas as well. GLS has been reported in Missouri, Iowa and Nebraska. This dramatic increase of locations having the disease is associated with no-tillage or reduced-tillage production methods. These conditions contribute to overwintering of the fungus and early infection the following season.

The fungal pathogen *Cercospora zeae-maydis* which causes GLS, characteristically produces long, rectangular, grayish-tan leaf lesions which run parallel to the leaf veins. These lesions may blight the entire leaf. Blighting due to GLS is associated with the premature loss of photosynthetic area. The dominant sink of the post-flowering maize plant is the ear. Blighting induces the plant to transfer photosynthate from the stalk and roots to the ear at high levels causing premature senescence.

The level of resistance to GLS in commercial hybrids and inbreds has been evaluated. Resistant or tolerant genotypes have been reported but few, if any, can be classified highly resistant. Although there was little evidence of any strong resistance to GLS in the commercially available hybrids, potential sources of resistance in several inbred lines (Va59 and Pa887p) have been reported. The Pennsylvania State University Experiment Station has released an inbred, Pa875, with resistance to GLS which appears to be multigenic and additive in nature. This inbred is a good source of resistant material, but it does not solve the GLS problem. There is a need for commercially acceptable hybrids which are GLS resistant. And there is a remaining need for an easy and trackable method of development of other resistant maize inbreds and hybrids.

In an article by D. M. Bubeck, M. M. Goodman, W. D. Beavis and D. Grant, 1993, entitled Quantitative Trait Loci Controlling Resistance to Gray Leaf Spot in Maize, Crop Sci.33:838–847, the authors presented one loci for GLS which was consistent and numerous loci for GLS which were inconsistent. On the other hand, the present invention teaches four consistent loci for GLS. Thus, the present invention is not specifically taught. This article attempted to identify quantitative trait loci (QTL) on the basis of marker associations with GLS means over all ratings taken in environments. The paper indicates the use of RFLP mapping of two different donors having partial resistance to GLS (ADENT and NC250A) in three populations. The reference shows that the QTL were inconsistent over environments. Although this paper leads to the conclusion that the practical use of markers is limited because of environmental influence which gives inconsistent results; the paper recites a breeding application. The paper indicates selection should be based on the phenotype and the genotype of the inbred. It should be noted that Table 8 in the paper indicates that the marker association would have led to the selection of nine families which rated poorly for GLS in a visual rating.

The paper indicates a number of identified GLS loci which seem to vary by environment. The present invention, on the other hand, clearly identifies loci of Va14 which remains consistent throughout environments. Additionally, the present invention teaches a method of improving GLS susceptible inbred lines by selecting for the genotype identified by markers of the desired targeted inbred and selecting for the introgression of the Va14 material at the selected loci. This invention clearly covers an inbred that has targeted inbred material in substantially all chromosomal regions except at least one or more of those identified as loci 1–4. In this invention at least some of the loci 1–4 in the chromosomal regions contain the introgressed GLS resistant material. This invention is not taught by the above identified reference.

Unfortunately, due to the genetics of GLS resistant maize, it is difficult to transfer this resistance to new inbreds. And it is difficult to transfer it to new hybrid products. In fact, it is quite common to see some poor agronomic traits and loss of resistance associated with moving the resistance trait from inbred to inbred.

Heretofore, few if any, truly agronomically desirable varieties of corn have resistance to GLS. This invention discovered that four chromosomal regions control the maize plant's response to the GLS in Va14. A progeny containing these genes, two of which are recessive in nature, within its genome is expected to be a rare occurrence.

Maize breeding combines two inbreds to produce a hybrid having a desired mix of traits. Getting the correct mix of traits from two inbreds in a hybrid can be difficult, especially when traits are not directly associated with phenotypic characteristics.

In a conventional breeding program, pedigree breeding and recurrent selection breeding methods are employed to develop new inbred lines with desired traits. Maize breeding programs attempt to develop these inbred lines by self-pollinating plants and selecting the desirable plants from the populations. Inbreds tend to have poor vigor and low yield; however, the progeny of an inbred cross usually evidences vigor. The progeny of a cross between two inbreds is often identified as an $F_1$ hybrid. In traditional breeding $F_1$ hybrids are evaluated to determine whether they show agronomically important and desirable traits. Identification of desirable agronomic traits has typically been done by breeders' expertise. A plant breeder identifies a desired trait for the area in which his plants are to be grown and selects inbreds which appear to pass the desirable trait or traits on to the hybrid. Conventional plant breeders rely on phenotypic traits of the inbreds for selection purposes.

Modern plant breeding technology looks at the genotypic material (chromosomes) for plant breeding purposes. One method of looking at plant genotypes is to use Restriction Fragment Length Polymorphisms (RFLPs). RFLPs can be used to identify the chromosomal regions which affect the agronomic traits in the plant genome. The plant breeder can use this information to introgress the trait into the inbred line for ultimate expression in the hybrid.

Maize is a ten chromosome plant. Each chromosome has a short arm with a distal and proximal end and a long arm having a distal and proximal end. The short arm proximal end and long arm proximal end define the edges of the centromere. Each chromosome is made up of strands of the deoxyribonucleic acid (DNA) molecule which has a specific nucleic acid sequence. Selected restriction endonucleases will identify a specific base sequence and cleave the DNA molecule wherever this sequence occurs. The resultant cleaved portions are called restriction fragments. These restriction fragments can be separated by size by electrophoresis through agarose gels.

The DNA of two individual maize plants will differ in sequence at a variety of sites. Because of this difference, restriction endonucleases may cleave the two plants' DNA at a different sites. A polymorphism in the length of restriction fragments is produced when the fragments of the two plants have different lengths. A polymorphism is detected by placing the fragments on an agarose gel electrophoresis and allowing them to separate by size over distance. A Southern blot is then used. The fragments of the DNA are physically transferred on to a membrane, then nucleic acid hybridization detects the sequences by hybridization of the single strand of DNA (probe) on the Southern blot. The nucleic acid reforms double stranded DNA. A probe is used to detect a particular (DNA) sequence. One detection method uses autoradiography.

A variety of maize genes have been mapped and identified using RFLPs. Certain molecular markers are used to identify chromosomal areas associated with certain traits. A large number of molecular markers including RFLPs have been applied to the maize genome. A detailed maize genetic map has been constructed.

A variety of traits has been identified by RFLPs; for example, pericarp color has been linked to UMC185(P1) on the short arm of chromosome one of the maize plant. Probes BNL6.29 and UMC85 on chromosome six of the maize plant have been identified with Maize Dwarf Mosaic Virus (MDMV) strain A resistance in maize. Likewise, a variety of other traits have been genetically identified and placed on the maize genetic linkage map.

It is not easy to recognize the desired chromosomal location of a desired trait. Although RFLPs are a tool which can be employed to help identify the chromosomal region to which the trait appears to be linked, RFLPs are not a solution in and of themselves. RFLPs are simply a tool of identification. It should be noted that all of these specific chromosomal regions associated with GLS resistance have not been previously mapped or identified using probes.

Little has hitherto been known about the genes responsible for resistance to GLS, except that GLS resistance seemed to be additive in nature and difficult to carry into new plants. The present invention allows selection of progeny which contain the genomic background of the agronomically desirable parent and the genomic trait of the GLS donor parent. There is a need for the identification of these specific locations of genes associated with resistance to GLS to permit their tracking. Tracked material can be introgressed into new plants through traditional breeding. There also remains a need for a method of transferring resistance to GLS to corn inbreds having desirable agronomic traits and adapted for various regions where GLS is found. There remains a need for resistant GLS inbreds and hybrids.

SUMMARY OF THE INVENTION

An object of the present invention is to provide a maize line which exhibits resistance to GLS and maintains other agronomically desirable traits in hybrid combination.

A further object of the invention is to provide a commercially viable GLS resistant hybrid.

Still another object of the present invention is to provide a GLS resistant inbred which contains Va type material therein at set loci.

Yet another object of the present invention is to provide a method to identify and track chromosomal regions when breeding plants to develop resistance to GLS in the progeny.

Broadly then the present invention is an improved inbred maize line, being derived from a first parent which evidences a resistance to GLS and a second parent which evidences a susceptibility to GLS and has germplasm with desirable yield characteristics, and wherein the improved inbred line has the resistance to GLS, not significantly less than that of the first parent and yield characteristics which are not significantly less than those of the second parent.

Furthermore, the present invention includes an elite inbred maize plant and parts thereof, exhibiting resistance to GLS, comprising a genome which is homologous in respect to genes within identifiable chromosome regions conferring resistance to GLS derived from the resistant parent and genes specifying desirable agronomic traits when in hybrid combination, the genome being entirely of maize origin.

More specifically then the present invention encompasses a maize plant resistant to GLS, the genome which contains genes associated with resistance to GLS at, one or more loci selected from the group consisting of: (locus 1) chromosome 1, between map unit 124 and map unit 135; (locus 2) chromosome 2, between map unit 64 and 91; (locus 3) chromosome 5, between map unit 90 and map unit 103; (locus 4) chromosome 8, map unit 129 through map unit 136; references to map units and chromosomal location being references to the chromosome map published for the 1993 Maize Genetics Cooperation Newsletter Mar. 15, 1993, at FIG. 3.

Additionally, the present invention is related to the production of hybrids using converted inbreds or progeny of the converted inbreds. Thus the present invention includes a maize hybrid plant, or plants, parts of the plant progeny of the cross between first and second inbred lines, at least one of the inbreed lines being a converted line, with the genes conferring resistance to GLS being present in homologous state in the genome of one or the other or both of the first and second inbred lines such that the genome of the first and second inbred lines together donate to the hybrid a complement of GLS genes necessary to confer the resistance to GLS to the hybrid.

The present invention further includes a method for production of inbred maize plants adapted for conferring, in hybrid combination with a suitable second inbred, resistance to GLS. The method includes the steps of first selecting a donor parent line possessing the desired GLS resistance trait and crossing the same with an elite, high yielding second parental line to produce a segregating population; screening the plant population for the identified chromosomal loci having one or more genes associated with the resistant trait; selecting from the population plants having the identified chromosomal loci for further crossing and selection, and repeating the crossing and selection until the line is obtained which is homozygous for the resistance trait at the selective loci and has the necessary elite, high yielding genotype to give agronomically acceptable characteristics in hybrid combination.

The present invention further includes a variety of new inbreds including ZSGLSF1 and ZSGLSMu. ZSGLSF1 is shown in hybrid B in FIG. 2 which is resistant to GLS.

These and other objects of the present invention will become more readily appreciated and understood from a consideration of the following detailed description of the preferred embodiment when taken together with the accompanying drawings, in which:

BRIEF DESCRIPTIONS OF THE DRAWINGS

Figure 1:
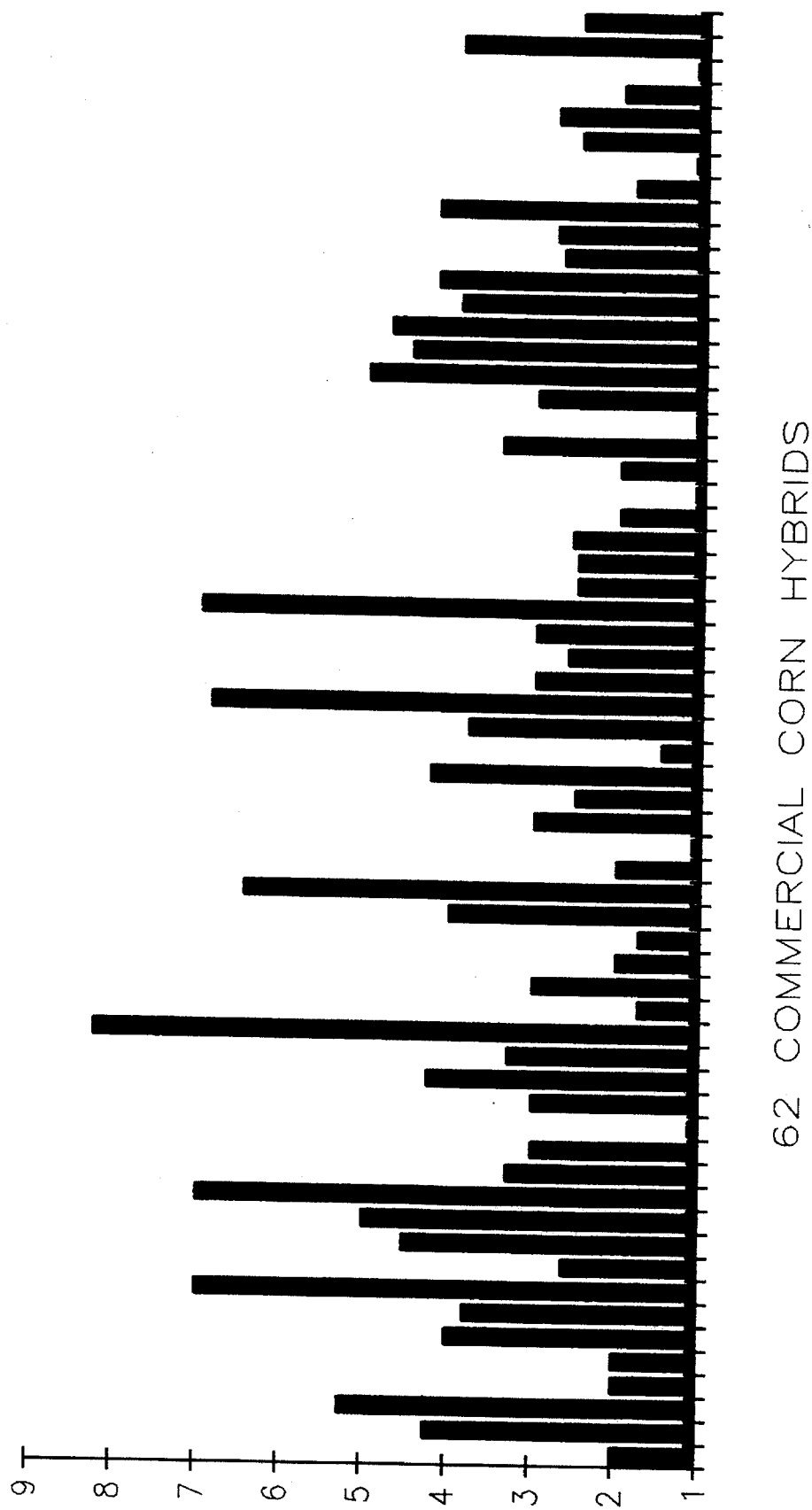
FIG. 1 shows a point rating scale comparing the various prior art commercial hybrids' GLS resistance levels.

FIGS. 3A-1, 3A-2, 3B-1, 3B-2, 3C-1, 3C-2, 3D-1, 3D-2 are a map listing probes for the chromosomes of the maize plant. The map shown is from the map published by the 1993 Maize Genetics Cooperation NewsLetter published Mar. 15, 1993, by Department of Agronomy and U.S. Department of Agriculture, University of Missouri, Columbia, Mo.

FIG. 4 is a table of data indicating the magnitude of statistical significance of the rating score differences of homozygous RFLP genotypes for each pair of RFLP probes;

FIGS. 5A, 5B, 5C, 5D show the original mapping of the gene action and chromosomal regions associated with the four GLS genes;

DETAILED DESCRIPTION OF THE EMBODIMENTS

Broadly this invention relates to a maize plant and a method of producing the same, which is resistant to GLS. This invention relates to the introgression in maize of genetic material which is capable of causing the plant to be resistant to GLS. Additionally the present invention relates to the method of introgressing the desired GLS genetic material from one or more parent plants into the progeny with precision and accuracy. It should be appreciated that the GLS resistant converted lines such as ZSGLSF, ZSGLSMu or Va14/B73 offers a much improved donor for use in pedigree or backcrossing programs because the recombination of genes for yield and other desirable agronomic traits have already been accomplished by the present invention. To assist in the description of this invention the following glossary of terms are provided.

| | |
|---|---|
| Converted Plant - | any plant having resistance to GLS derived from Va14, a progenitor or a progeny thereof, and which is a plant or has an ancestor which was or has been selected by reference to RFLP data for at least one of the loci herein defined as locus 1–4. |
| Crossover - | shall mean an exchange of segments of homologous chromosomes during meiosis whereby linked genes become recombined; also the product of such an exchange. The cross-over frequency is the proportion of gametes bearing a cross-over between two specific gene loci. it generally ranges from 0 for allelic genes to 50% for genes so far apart that there is always a cross-over between them. The cross-over site is the place in the chromosome where breakage and reunion of DNA strands occur during recombination. |
| Introgression - | shall mean the entry or introduction of a gene or a linkage block from one plant into another. |
| Introgressing - | shall mean entering or introducing a gene or a linkage block from one plant into another. |
| Linkage Block - | shall mean an identified chromosomal region containing genetic material that expresses a desired trait. |
| Recombination - | shall mean reassortment of genes or characters in combinations different from what they were in the parents, in the case of linked genes by crossing over. |

The method of the present invention comprises use of molecular markers to select progeny from a cross between a GLS resistant donor and a susceptible recipient. The selected progeny contains all or most of the preferred alleles for GLS resistant maize and many agronomically desirable traits. It is not necessary and often inefficient to find the complete complement among the progeny of a first cross. However, it is possible to select individual progeny plants exhibiting a proportion of the desired recombinations and to further cross or backcross such individuals in order to create the desired genome progressively.

The donor parent is preferably a line designated Va14 or a plant from the same plant population as Va14 or its progenitors or resistant progeny which contain the loci 1 through 4 (described below) which are detectable by RFLP or equivalent molecular marker analysis. The donor of the GLS resistant genetic material used in the present invention is a public line released by Virginia Polytechnic Institute and State University. Other sources of this genetic material will of course be located since the present invention now allows this material to be identified. Additionally the identified chromosomal regions can readily be analyzed by use of a yeast artificial chromosome library or other gene library to identify and specifically sequence the genes contained therein. These genes can then be used in a cloning protocol for introgression into new plants by transformation techniques such as particle bombardment, whiskers, microprojectile introduction or Agrobacterium.

The present invention has the entire yield/GLS resistant package and includes a method of using modern breeding techniques to move the desirable genetic material from one elite background to other elite backgrounds or from germplasm source material to elite backgrounds, etc.

This invention was developed in two stages. The first stage was the location of the chromosomal regions containing genes that characterize that plant as expressing resistance to GLS. The second stage was the introgression of the identified chromosomal regions into a female and male genotype that have agronomically desirable traits so that resistant hybrids can be produced.

The steps taken to develop the invention are as follows:

1) R×S crossed to develop resistant and susceptible progeny (R=resistant material, S=targeted inbred);

2) Selfing to produce a genetically segregating population;

3) rating the resulting GLS level of each plant of the segregating population;

4) analyzing the RFLP data of the plants rated as resistant with the RFLP data of the plants rated susceptible to determine the gene action in the chromosomal regions associated statistically with resistance; (This completes stage 1.)

5) Transfer the regions indicated in the resistant parent into a commercially elite susceptible parent and confirm resistance and gene locations.

6) Breeding: with the progeny, and/or using a new susceptible plant to form a new population. Selecting plants from a) or b) with RFLP backgrounds similar to the susceptible plant with the introgressed chromosomal regions from the resistant parent. (Stage two). Confirmed locations and resistance in two elite parents.

The population used to establish the chromosomal regions had R=Va14 and S=B73 (available from Iowa State University). Once the chromosomal regions were located, various S's were used. Due to the recessive gene action in two of the chromosomal locations, a hybrid would preferably have these recessive genes in both parents. To maximize the GLS level in the hybrid at least one GLS resistant inbred for male use and at least one GLS resistant inbred for female use were developed. In more detail, stage one is described below.

To begin stage one there should be a means to assess the plants' level of resistance to GLS. Historically resistance assessment of GLS on plants has been based on visual observation. The present invention was rated using a visual scoring scale as shown in Table 1, but with increments of 0.25.

Table 1: GLS Scoring Scale

0=no symptoms

1=trace of lesions below the ear

2=large lesions below the ear

3=large lesions below the ear and all leaves above the ear have some lesions

4=all leaves have large lesions, but green leaf area remains

5=all leaves dead

The historical scoring scale was not precise. Thus, the rating scale used was even more graduated and scored by increments of 0.25. Thus a plant between a 3 & 4 rating would rate 3.25, 3.50 or 3.75 depending on whether it was closer to a 3 or a 4. This precise rating system Plant Dis. 77:583– 587,199) was used at Whitethorne Research Farm (Virginia Polytechnical Institute and State University (VPI & SU))in Virginia. This farm over years has shown substantial GLS pressure.

The inbred line Va14 was developed at VPI & SU and has the following pedigree (VaCBS SEL×Va17) Va17. A different rating scale (1–9, 9 best) was used to assess commercial hybrids (FIG. 1) and inbreds prior to the more accurate GLS scoring experiments described above. The genetic background of Va14 demonstrates a high degree of resistance to GLS, a rating of 8 on a 1–9 scale, where 1 is highly sensitive and 9 is highly resistant (almost symptomless). In contrast the "S" (sensitive) line, the B73 line, used for identification of the chromosomal regions of interest rated 1 on the 1–9 scale.

Attempts by breeders to convert the sensitive GLS lines to GLS resistant lines by traditional breeding techniques have been largely unsuccessful. Traditionally, developed inbreds which used Va14 as a donor parent often result in lines which possess agronomic traits of the sensitive lines without high levels of GLS resistance. FIG. 1 shows the resistance levels of a number of commercial hybrids. Most of these commercial hybrids have a rating below 4. It is believed traditional breeding methods lose GLS resistance because of the recessive nature of some of the GLS genomic material. The present invention overcomes this problem.

To form a GLS hybrid, a population was developed by crossing Va14=R (resistant GLS source) by B73=S (a susceptible GLS source). The screening procedure allowed the identification of the extreme tails of the "R"×"S" $F_2$ populations. In other words, plants which were extremely susceptible and plants which were extremely resistant to GLS were identified.

The table in FIG. 4 shows information derived from experiments on the B73/Va14 $F_2$ and $F_3$ populations. It was discovered that GLS resistance is associated with four chromosomes. These are chromosomes 1, 2, 5, and 8. The gene action on chromosomes 1 and 2 is additive and on 5 and 8 is recessive. Additionally it was noted that the susceptible source B73 has some resistant chromosomal material on chromosomes 3, 4 and 7. The B73 resistance does not contribute a major effect and are not included in the best mode of the invention; but, portions of the B73 background may slightly increase resistance.

The RFLP data shown in FIG. 4 was generated by the following RFLP protocol and/or by the protocol outlined in the article "Ribsomal DNA Spacer Length Polymorphisms in Barley: Mendelian Inheritance, Chromosomal Location, and Population Dynamics." which is written by Saghai-Maroof, M. A., K. M. Soloman, R. A. Jorgensen, and R. W. Alluld. 1984. Proc. Natl. Acad. Sci., U.S.A. 81:8014–8018.

A. DNA Extraction

The corn plant tissue from each tail was excised from growing plant and lyophilized, ground to a fine powder in a mill and the DNA was extracted. 100 µl of RNase (10 mg/ml) were placed in tubes and the supernate was filtered and placed in the tubes and incubated. The DNA precipitate was snagged, transferred to a culture tube containing 76% ETOH/10 mM NH$_4$Ac, and incubated. See Proc.Natl. Ac.Sci. USA 81:8014–8018

B. DNA Digestion

The DNA was quantified fluorimetrically, and digested to completion. DNA was loaded into an agarose slab gel and electrophoresed. DNA was transferred onto Hybond-N+ membrane (Amersham) via southern blotting. The protocol used is the protocol suggested by the manufacturer.

C. Southern Blotting

A 25 mM NaH$_2$PO$_4$ pH=6.5 transfer buffer was used. The Southern Blot procedure is well known in the art at J. Mol. Biol.98:503 (1975).

D. Oligo Reaction

40 µg DNA was mixed with sufficient H$_2$O to make up 3 µl of solution. The DNA was denatured for ten minutes at 95° C. and then 10 µl oligo buffer, 2 µl BSA, 5 µl 32P-dctp, 2 µl Klenow was added. The sample was incubated and then a 150 µl stop buffer was added. This protocol is published in Feinberg, A. P.,B. Volgelstein, Anal. Biochem. 132:6,1983.

E. Probe Hybridization

Probe fragments were generated from recombinant plasmids using SDS Lysis isolation procedure and the products gel-purified for labelling with 32p-dctp (Amersham) via random priming. The blots were decanted and placed on Kodak XAR X-ray film and exposed. The procedure used is published in B. Buddowle, et.al. Crime Laboratory Digest 15:3–21, 1988.

F. Probe Removal

The blots were washed in 5 mM Tris-HCL/pH 8.0, 0.2 mM EDTA 0.05% pyrophosphate, 0.1×Denhart's for 1–2 hours at 65°–75° C. Denhart's Solution (50×) is formed as follows:

Ficol—5 g, polyvinylpyrolidone—5 g, BSA (Pentax Fraction V)—5 g, H$_2$O—500 ml. blots were then rinsed in 1×SPE. SSPE (2×) is formed as follows: 174 g NaCl, 27.6 g $NaH_2PO_4$ $H_2O$, 7.4 g EDTA, 800 ml $H_2O$, adjust to pH 7.4, bring volume to 1 liter.

The data in FIG. 4 were produced when determining the chromosomal regions having resistance and the regions that identified the sensitive background. These data show that a large number of probes were used on the four chromosomal regions of interest to precisely define the location of the resistant material. GLSF2 and GLSF3, are two different ratings, for $F_2$ and $F_3$ plants respectively, of the population of Va14=R/S, using the precise GLS scoring scale (0–5 by 0.25 increments). The chromosomal regions associated with resistance to GLS were located by comparing scores of the plants in the homozygous susceptible (SS) and resistant (RR) RFLP classes. Approximately 230 plants were used to generate the data shown in FIG. 5. The RFLP linkage analysis identified locations of four major genes (two additive dominant, two recessive).

FIG. 4 shows the results of a method of statistical analysis on the RFLP and GLS scoring data of these 230 plants. The data resulting from the above procedure were analyzed locus-by-locus with analysis of variance as proposed by M. Soller, T. Brody and A. Genizi (1976, Theoretical and Applied Genetics 47:35–34). The Statistical Analysis System (SAS) package of programs was used for this data analyses. SAS is commercially available from: SAS Institute, Inc., SAS Campus Drive, Cary, N.C. 27513.

The plant source of the genetic material associated with the listed probes is indicated in FIG. 4. In FIG. 5 negative signs in the FALCA column indicate that the source of resistance is the resistant parent, no sign (i.e. positive) indicates the source is the susceptible parent.

| | |
|---|---|
| Rsq. = | estimated proportion of total variation associated with the RFLP probe based on the difference between rated symptoms of the homozygous resistant and homozygous susceptible allele classes. |
| PR>F = | probability of chance occurrence. |
| FALC A = | estimate of half the difference in true homozygous class means, Falconer's 'a' (D.S. Falconer, Introduction to Quantitative Genetics, Third Edition, 1989, Longman Scientific Technical). |

The probes are listed by their first letter and their number, i.e. probe BNL7.25 (as listed in FIG. 3) would be listed in FIG. 5 as BO725. Experiments were run using selected probes which are associated with the genetic material that evidenced resistant GLS response in the RR plant (genetic information associated with the probe indicates derivation from the resistant (Va14) plant). Results of the statistical analysis of the plant's rating at each probe location, based on the level of statistical significance, identified the four chromosomal regions of interest. Likewise, the background genome of Va14 and the susceptible plant are identified for future selection use.

Figures 1, 3A:
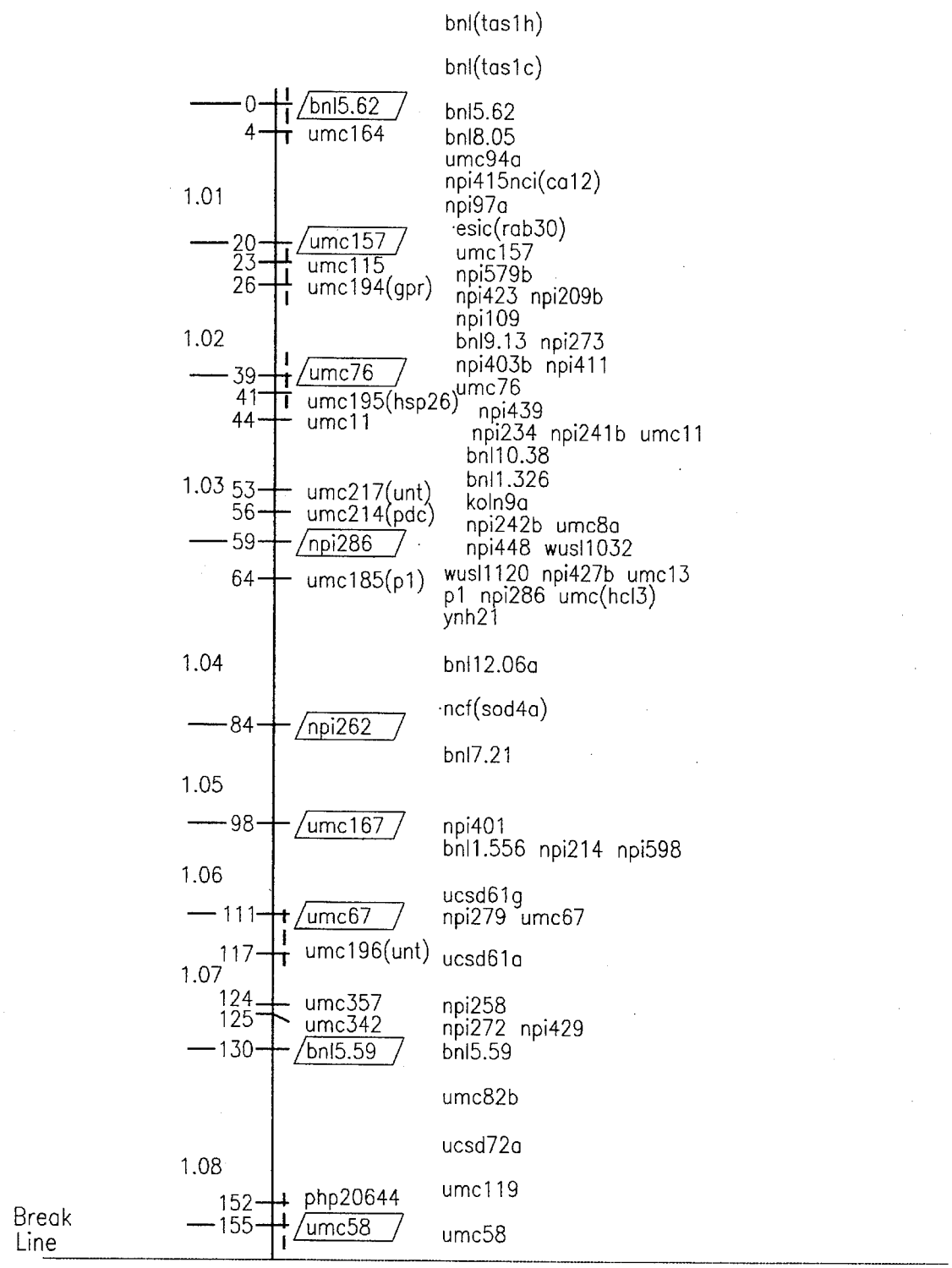
Figures 1, 3B:
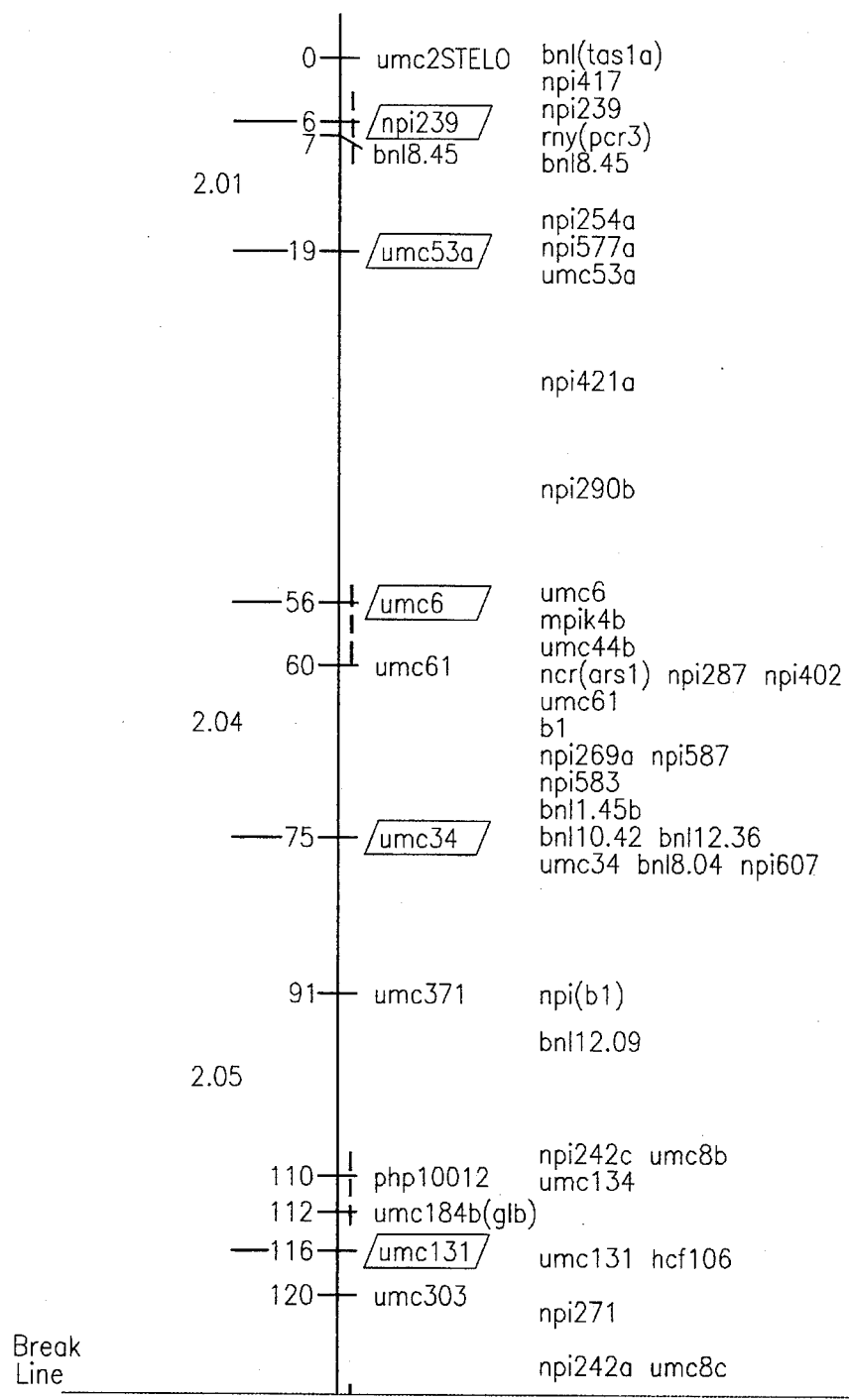
Figures 2, 3B:
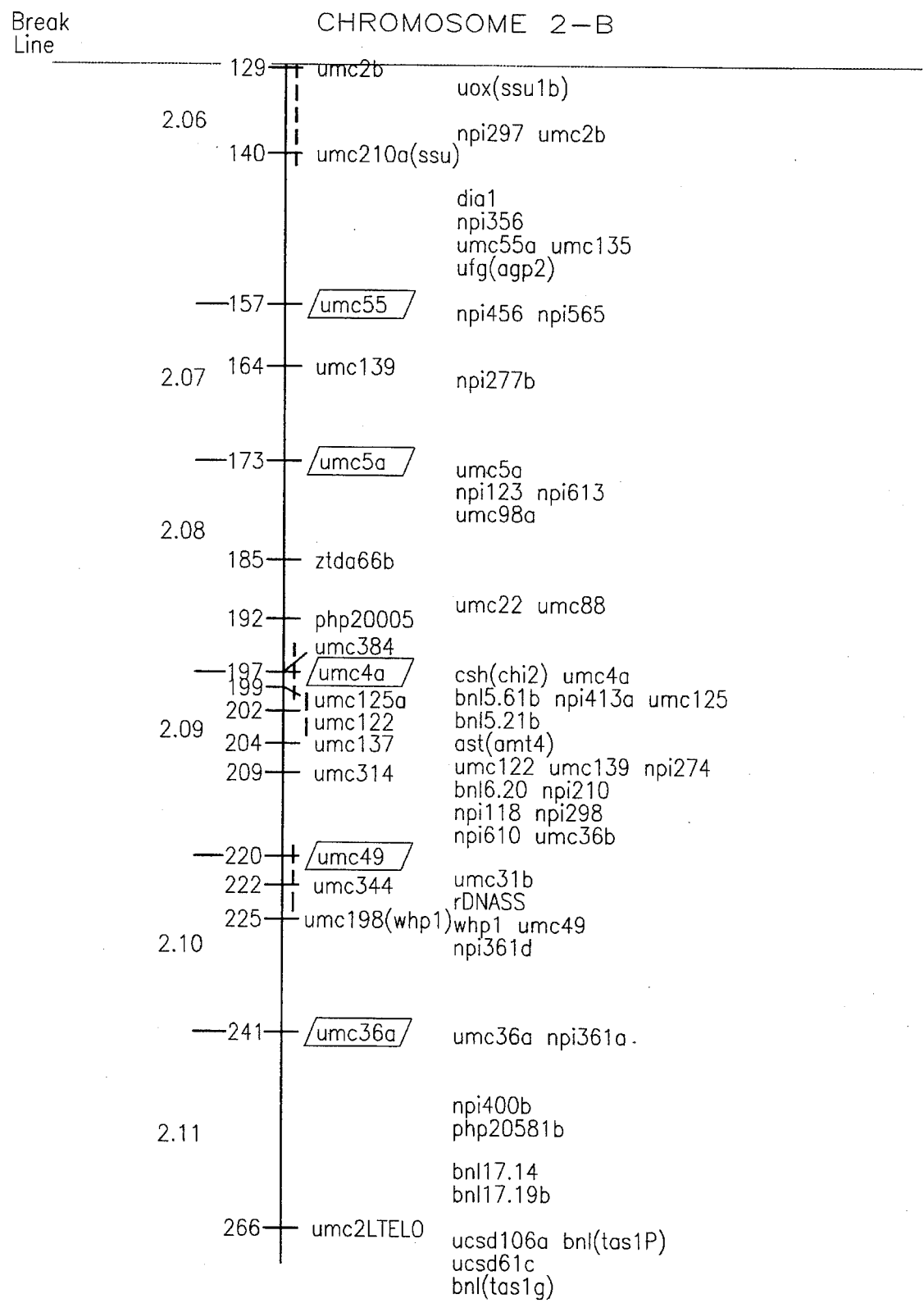
FIG. 2 is a chart comparing a commercially available hybrid designated "Z" with two inbreds in hybrid combination each made in accordance with the process of the present invention. These inbreds are crossed to the same inbred tester as is present in Hybrid Z.
Figures 1, 3C:
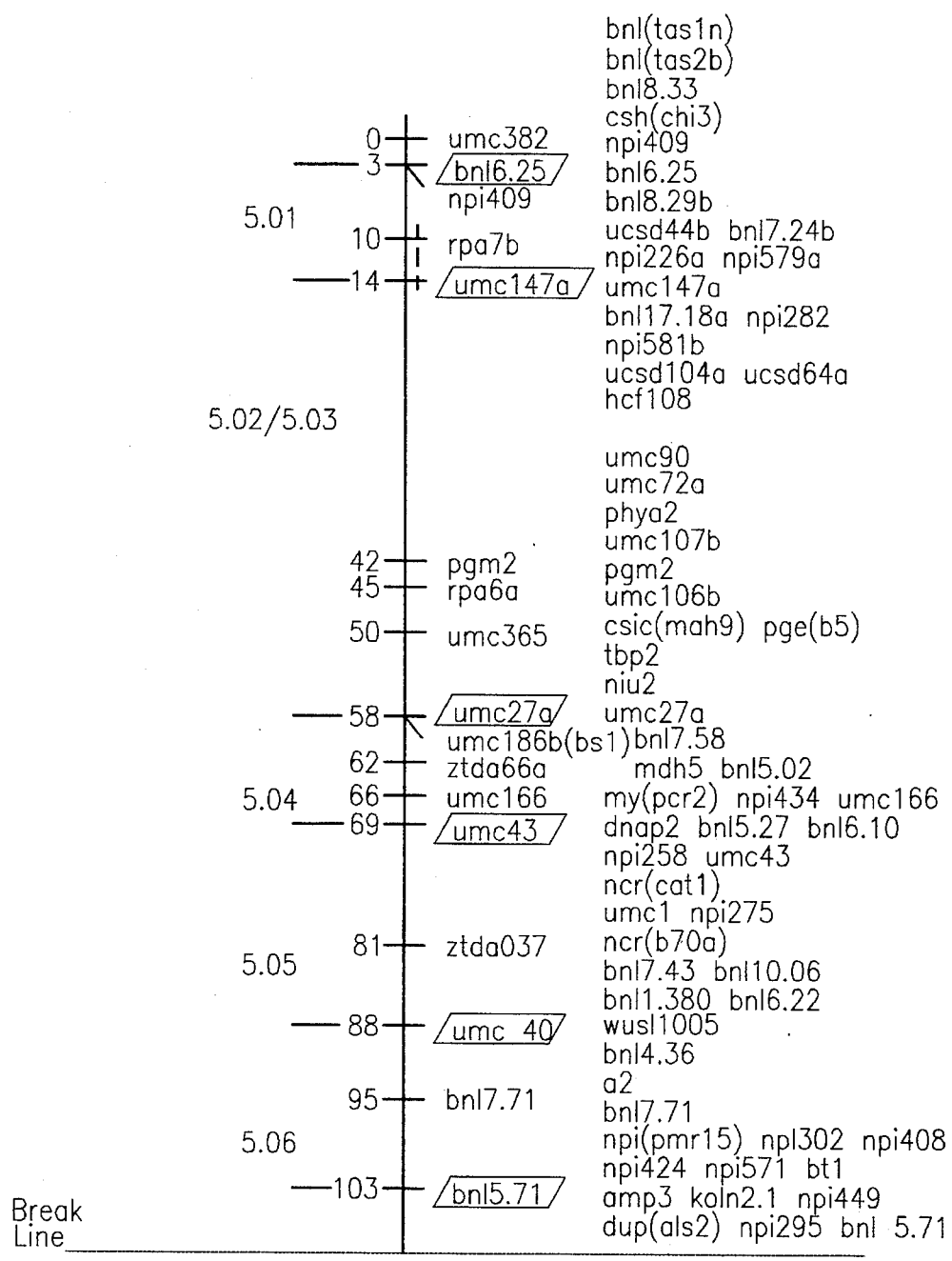
Figures 2, 3C:
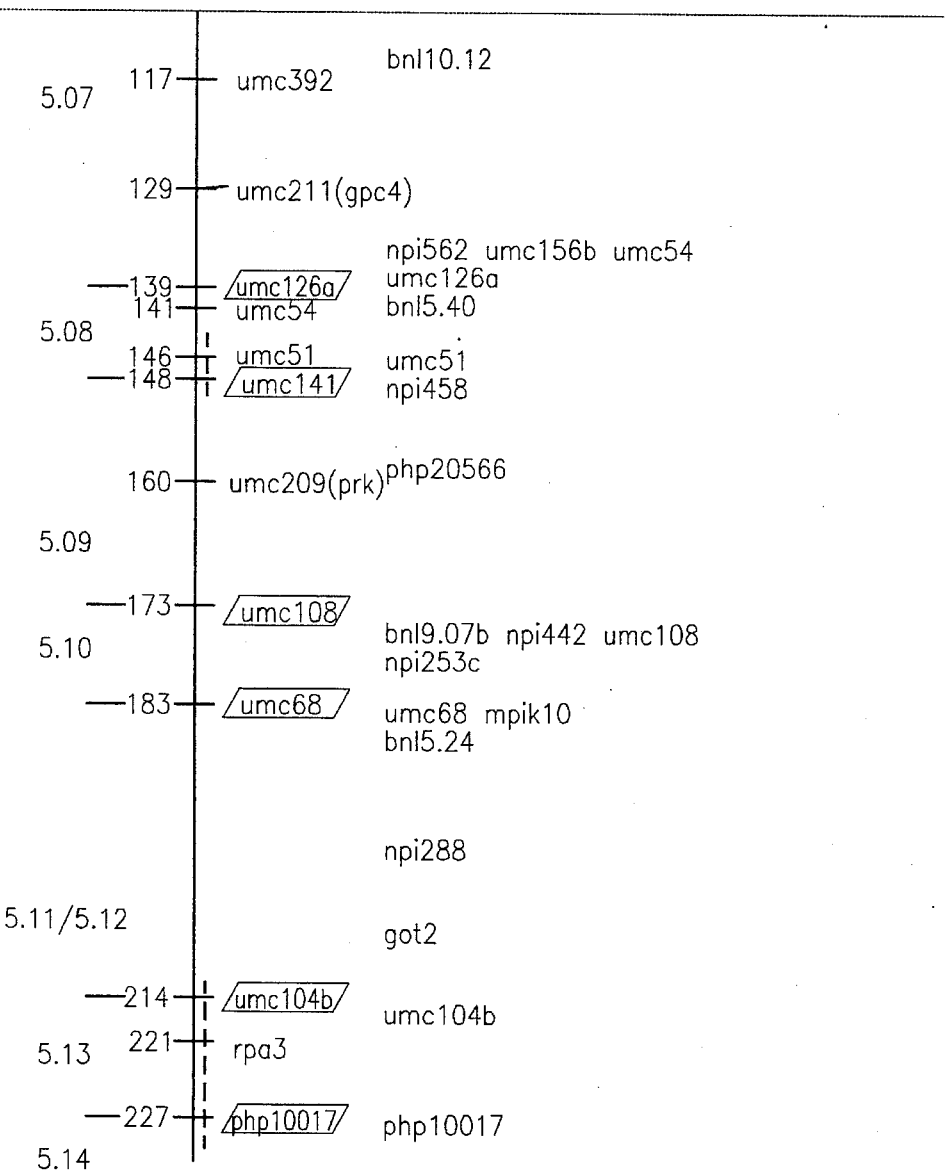
Figures 1, 3D:
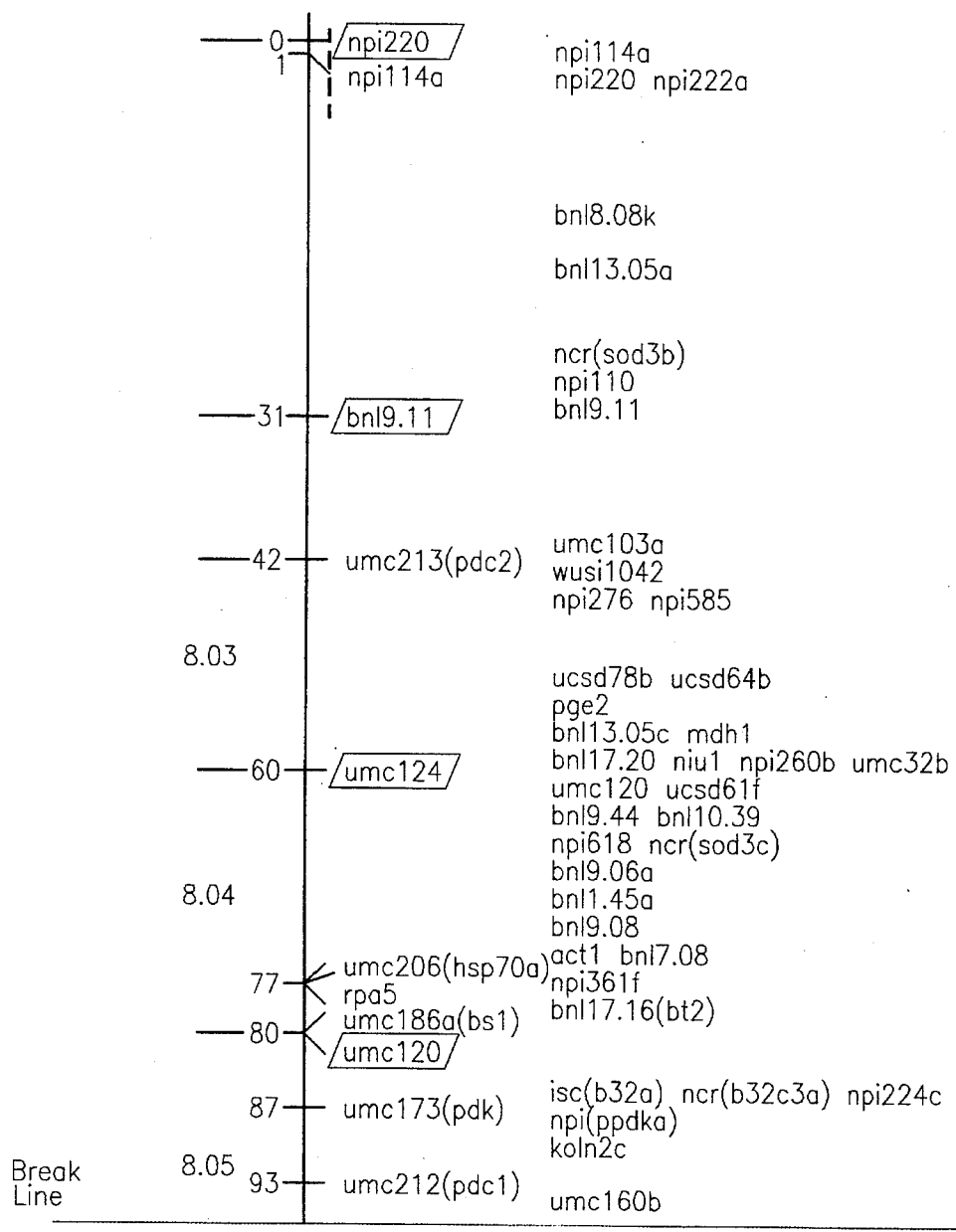
Figures 2, 3D:
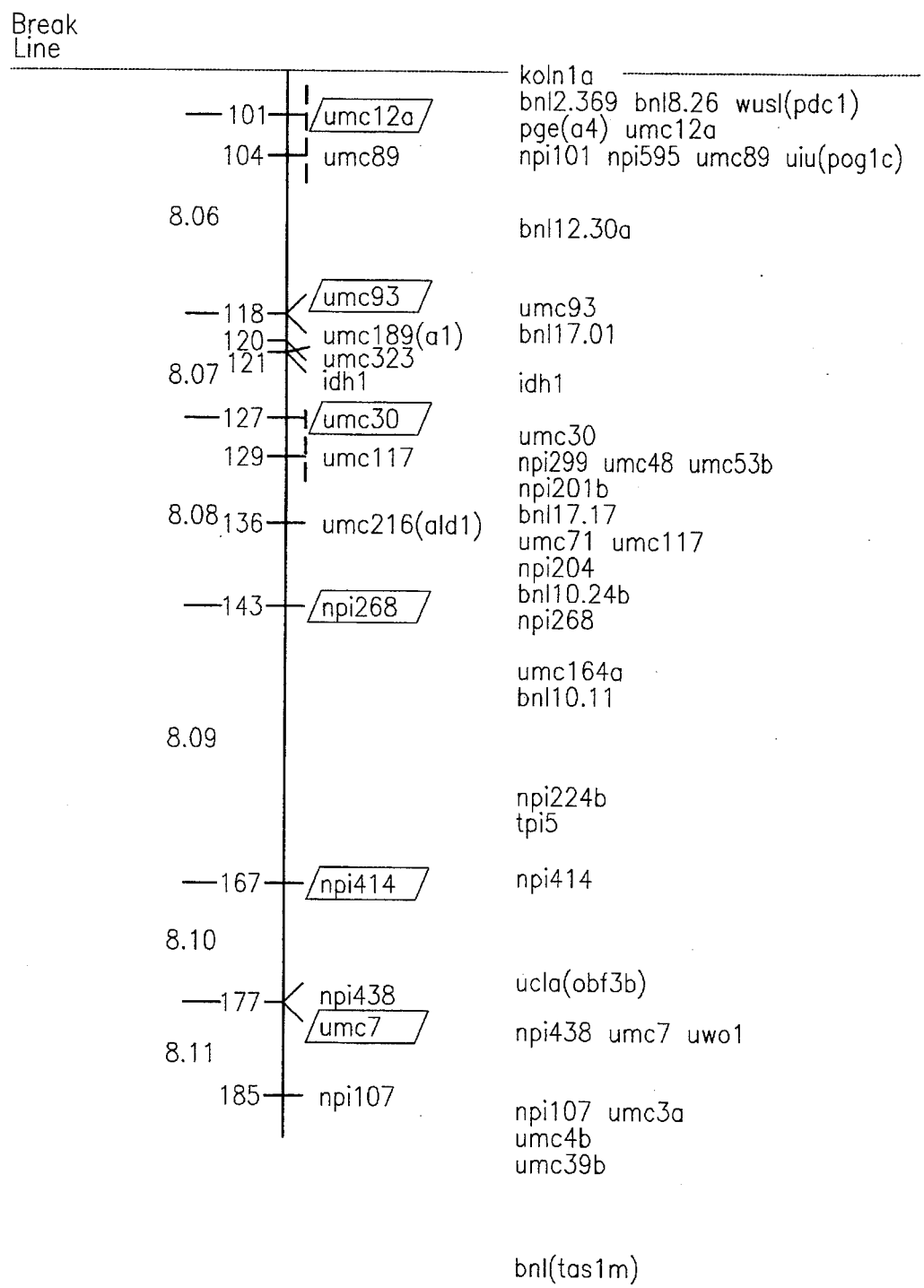

In addition to the data shown in FIG. 2, data were generated through the introgression of the trait into various targeted elite backgrounds. Major effects were observed from Va14 on chromosome 1 center; chromosome 2 short arm, and on chromosome 5 center-long, and on chromosome 8 long arm. The gene action of the regions on chromosomes 1 and 2 is additive to dominant and the gene action of the regions on chromosomes 5 and 8 is recessive. The B73 material on chromosomes 3, 4 and 7 can be selected and introgressed; but the effect of these regions is less important than that of the Va14 donor.

Through further generations of new probes identified even more closely the area between which lied the genetic material of interest. Regions of interest were more closely located in two populations and the combinations thereof. Population 89 shown in Table A is a cross between Va14 and an inbred developed from B73 (hereinafter B73 progeny). In Table A the positive Falc A shows the resistant parent and the negative indicates the susceptible parent. Population 89 clearly defined the regions of material on chromosomes 1 and 5 which had to be introgressed from Va14 to carry the GLS resistance.

TABLE A

| | | POPULATION 89 | | | |
|---|---|---|---|---|---|
| CHROM | PROBE | PR>f | RSO | FALC A | PR>T |
| 1 | AS067A | 0.01 | 0.14 | 3.68 | 0.01 |
| 1 | U0067B | 0.19 | 0.06 | 2.62 | 0.09 |
| 1 | N0279E | 0.01 | 0.13 | 3.66 | 0.01 |
| 1 | U0357B | 0.05 | 0.11 | 3.35 | 0.03 |
| 1 | U0342CB | 0.13 | 0.18 | 5.00 | 0.07 |
| 1 | B0559B | 0.20 | 0.06 | 2.40 | 0.13 |
| 1 | I01270 | 0.01 | 0.15 | 3.57 | 0.01 |
| 1 | N0358D | 0.01 | 0.13 | 3.57 | 0.01 |
| 1 | N0429B | 0.06 | 0.10 | 3.17 | 0.03 |
| 1 | U0058B | — | — | — | — |
| 5 | U0001B | — | 0.00 | | |
| 5 | B0436B | 0.00 | 0.22 | 3.90 | 0.01 |
| 5 | B0771A | 0.01 | 0.13 | 2.93 | 0.02 |
| 5 | N0295A | 0.05 | 0.12 | 2.09 | 0.15 |
| 5 | B0571B | 0.06 | 0.10 | 3.38 | 0.02 |
| 5 | N0562A | — | — | — | — |

Va14 = R
B73 progeny = S

Population 72 more clearly defined the regions of material on chromosomes 1 and 8 which could be B73 progeny without loss of the GLS resistance. This mapping of regions is shown in Table B (again a negative Falc A=susceptible parent B73 progeny).

TABLE B

| | | POPULATION 72 | | | |
|---|---|---|---|---|---|
| CHROM | PROBE | PR>f | RSO | FALC A | PR>T |
| 1 | AS067A | 0.70 | 0.01 | 0.99 | 0.41 |
| 1 | U0067B | 0.43 | 0.03 | 1.52 | 0.23 |
| 1 | N0279E | 0.60 | 0.01 | 1.25 | 0.31 |
| 1 | U0357B | 0.17 | 0.06 | 2.10 | 0.10 |
| 1 | U0342CB | 0.38 | 0.04 | 1.38 | 0.36 |
| 1 | B0559B | 0.11 | 0.06 | 2.26 | 0.06 |
| 1 | I01270 | 0.11 | 0.06 | 2.40 | 0.05 |
| 1 | N0358D | 0.04 | 0.09 | 2.50 | 0.06 |
| 1 | N0429B | 0.04 | 0.09 | 2.77 | 0.02 |
| 1 | U0058B | — | — | — | — |
| 8 | N0426B | 0.01 | 0.24 | 5.69 | 0.00 |
| 8 | U0030D | 0.00 | 0.27 | 5.06 | 0.00 |
| 8 | U0048B | 0.00 | 0.19 | 4.64 | 0.00 |
| 8 | U0071 | 0.00 | 0.28 | 5.20 | 0.00 |
| 8 | U0117G | 0.32 | 0.03 | 1.67 | 0.19 |
| 8 | N0268B | 0.01 | 0.14 | 3.96 | 0.00 |

Va14 = R
B73 progeny = S

The combination of these populations data in the above Tables A and B led to the fine mapping of the linkage blocks. Clearly pinpointing the area of the GLS gene locations. The closest mapping of probes are as follows: Linkage block one, locus 1, is the genetic material located between Map Unit 124 and Map Unit 135 proximate probes UMC357 (now designated (CSU92) - ICI127 on chromosome one.

Linkage block two, locus 2, is the genetic material located between map unit 64 and map unit 91 proximate probes NPI269A -BNL12.09 on chromosome 2.

Linkage block three, locus 3, is the genetic material located between Map Units 90–103 proximate probes BNL4.36 BNL-5.71 on chromosome 5.

Linkage block four, locus 4, is the genetic material located between Map Unit 129 and Map Unit 136 proximate flanking probes UMC48-UMC71 on chromosome 8.

The donor parent Va14 carries significantly non-desirable agronomic characteristics. Thus it was necessary to identify the chromosomal regions of interest as closely as possible. This permitted introgression of Va14 material at specific linkage blocks 1–4 into the new elite germplasm. The crosses are selected by comparing the targeted elite fingerprint or probe pattern with the crosses having the Va14 material in the desired areas. Thus, the genome of the resultant inbred and likewise hybrid combination carried substantially all the elite background and only the linkage blocks of resistant material. Thus to generate a commercially viable inbred, the beginning crossover event (the crossover closest to the distal end of the short arm of the respective chromosome) and the ending crossover event (the crossover closest to the distal end of the long arm of the respective chromosome) can occur with precision and accuracy and avoid carrying excessive genetic material from Va14 into the resultant inbred. Precision and accuracy allows the desired inbred to be developed to have the background of a targeted plant and only the GLS exogenous, i.e. material from Va14, material giving GLS resistance at the loci 1–4.

It should be readily understood in the art that the other probes which more closely map the linkage blocks as identified by the map units could be employed to identify the crossover events. The linkage blocks listed permit the resistance trait to be readily identified and introgressed into other germplasm material. Larger linkage blocks could likewise be transferred within the scope of this invention as long as the material introgressed is sufficiently tailored to avoid transfer of unwanted traits into the resultant plant. It is emphasized that this invention may be practiced using any molecular markers which locate in similar regions, provided that the markers are polymorphic for the cross. It will be appreciated that breeding efforts which seek to improve agronomic traits while attaining GLS resistance are empowered by the genes of the superior allele in these linkage blocks.

It should be understood that a variety of hybrids with this trait could be developed and seed therefore produced and sold to farmers for maize production in GLS prone areas as well as in other locations.

As stated herein, one of the objectives of this invention is to improve the resistance to GLS of elite breeding lines without substantially affecting their combining ability. The term "elite" is a term of the art and its meaning is well known. Many factors contribute to the elite nature of these breeding lines. But of these factors the yield, in hybrid combination, and the moisture content of the seed, percentages of root and stalk lodging are of greatest importance. In performing this invention, then, the introgression of the resistance trait can be monitored from generation to generation along with the progressive restoration of the genetic background of the non-donor parent if so desired. The best selections made by using RFLP fingerprinting ultimately require field testing under GLS pressure so that the resistance trait is confirmed as is the yield of the newly resistant line. Ideally, the product line should have the same combining ability and substantially the same yield as the targeted elite parent.

The principal feature of this invention is the transfer of genes from a relatively resistant donor to a relatively susceptible recipient. However, the level of resistance of the recipient lines may vary. The sensitive recipient, as in this case, may itself possess resistance genes which may usefully be retained in the genome of the improved lines.

By virtue of this invention it is now possible to use molecular markers to introgress the GLS trait from Va14, or from parent or sibling, or progeny thereof, into elite lines. The following example outlines the introgression of the identified linkage blocks into two inbreds. One inbred is useful as a male and the other is useful as a female. Both inbreds are a yellow dent corn. The introgression of the desired linkage blocks in an elite inbred resulted in two improved inbreds.

The following is a protocol for developing an inbred having the desired trait using traditional breeding but selecting based on the rating data in combination with RFLP data: on the homozygosity of the trait; and the similarity of the RFLP data to the RFLP data of parent of choice. BC1 means back cross one, BC1S1 means the backcross has been selfed once.

The protocol for the inbreds used as females (a number of females were developed) and for the inbreds used as males differed. The male inbred protocol appears to be more efficient. First, the male protocol will be described. BC1 screen: Approximately 400–500 BC1 were rated in a disease pressure environment. Based on rating data, the top 100–120 plants were selected. An RFLP screen was run on 100–120 BC1 selections to identify the 50–60 individuals with all four GLS genes (two of the major genes are recessive). The 50–60 individuals were screened for background genotype of "M" (the male inbred) in order to select the best individuals for backcrossing. Two or more can be selected. All 50–60 individuals would be backcrossed to form BC2 families.

BC2 screen: 200–250 seed from each of the selected two or more BC2 ears are grown and rated under disease pressure. Selected top 100–120 plants. RFLP screen to identify 50–60 plants with all four genes. Screen background genotype and select two or more individuals to self and backcross.

BC3 screen: 200–250 seed from each of two BC3 ears grown and the best 50–60 plants with all four genes are selected. Background genotype is screened and two or more plants should be selected for selfing and backcross.

BC4 screen: 200–250 seed from each of the selected two or more BC4 ears are grown and rated under disease pressure. Selected top 100–120 plants. RFLP screen to identify 50–60 plants with all four genes. Screen background genotype and select two or more individuals to self.

BC4S1 screen: Screen up to 200 seed from each of two selected BC4 selfed ears (BC4S1 seed). Select 8–10 plants with high background genotype levels and fixed at all four loci. The 8–10 fixed individuals will be identified using RFLP's and selfed. Test cross these 8–10 individuals to a second inbred made by the process listed above.

BC4S2 seed: BC4S2 seed will have a progeny test. Test BC4S1-hybrids under disease pressure, and evaluate for yield and agronomic data. If necessary, a BC5 can be made and BC5S2 seed can be further increased and test crossed. The resultant inbred was designated ZSGLSMu.

Va14 (as a male) was crossed onto an elite targeted inbred. The inbred will hereinafter be called "F". Va14×F was selfed and then BC1 was formed and plant 290 was selected by RFLP for the four loci and the background genotype. This BC1 was selfed and selected three times to form BC1S3. It was discovered that one of the gene locations had been lost. BC1S3 was then backcrossed to an earlier BC1S2 to restore the missing region. The selected plants were grown in disease pressure and rated and selected and selfed. The agronomic characteristics of the inbreds were tested and considered with the unconverted inbred "F". In the process of selecting inbreds according to the RFLP data, additional data are also collected and analyzed. Table 2 shows some of the data collected in inbreds from various populations which were still segregating. Clearly, the data shows a comparison of inbred yield between the plant F and the inbreds which have been crossed to the Va14 and selected for GLS resistance. The inbred shown in Hybrid B in FIG. 2 shows 26% greater yield than the unconverted F. Some other inbreds show yield loss, some show yield gain in the segregating state.

TABLE 2

| PEDIGREE | # OF DAYS TO 50% SHED | GDD (50–80) TO 50% SHED | # OF DAYS TO 50% SILK | GDD (50–86) TO 50% SILK | PLT. HT. | EAR HT. | SHED G>F>P | ANTHER Y/R/P/O | GLUME G/R/P/O | SILK Clr. Y/R/P/O |
|---|---|---|---|---|---|---|---|---|---|---|
| F | 76 | 1461 | 77 | 1482 | 71 | 29 | G | Y | R | Y |
| 72153 | 79 | 1521 | 83 | 1598 | 73 | 40 | G | R | R | Y |
| 72156 | 79 | 1521 | 82 | 1585 | 73 | 36 | G | R | R | Y |
| 89101 | 78 | 1500 | 80 | 1545 | 76 | 39 | F | R | R | Y |
| 89103 | 76 | 1461 | 78 | 1500 | 78 | 43 | G | R | G | Y |
| 89104 | 79 | 1521 | 82 | 1585 | 69 | 36 | F | R | R | Y |
| 89109 | 77 | 1482 | 80 | 1545 | 74 | 38 | G | R | R | Y |
| 895610 | 80 | 1545 | 85 | 1628 | 73 | 41 | G | R | 16R/2 Y | Y |
| 895619 | 81 | 1565 | 85 | 1628 | 69 | 34 | G | R | R | Y |
| 89569 | 82 | 1585 | 84 | 1612 | 70 | 35 | G | R | R | Y |
| 8982 | 79 | 1521 | 84 | 1612 | 67 | 31 | G | R | R | Y |
| B 8985 | 80 | 1545 | 84 | 1612 | 68 | 35 | G | R | R | Y |
| 8987 | 80 | 1545 | 84 | 1612 | 70 | 34 | G | R | R | Y |
| 8988 | 79 | 1521 | 84 | 1612 | 73 | 36 | G | R | R | Y |
| 8989 | 82 | 1585 | 84 | 1612 | 82 | 45 | G | R | R | Y |
| 89810 | 82 | 1585 | 83 | 1598 | 76 | 33 | G | R | R | Y |
| 89811 | 81 | 1565 | 82 | 1585 | 74 | 38 | G | R | R | Y |
| 89815 | 81 | 1565 | 84 | 1612 | 70 | 36 | G | R | R | Y |

Pedigree = The entry name
# of Days to 50% Shed = The number of days from planting to 50% pollen shed
GDD (50–80) to 50% shed = The number of growing degree day units (50–80) from planting to 50% shed.
Of days to 50% silk = The number of days from planting to 50% silk.
GDD (50–86) to 50% silk = The number of growing degree day units (50–86) from planting to 50% silk.
Plant Height = Height in inches from the ground to flag leaf, collected from milk-dent stage.
Ear Height = Height in inches from the ground to the primary ear node.
Shed = Collected at 50% shed. G = good, F = fair, P = poor
Anther = The color of an extruded anther, Y = yellowish, R = reddish, P = purplish, O = other.
Glume = The color of the glume ring, G = greenish, R = reddish, P = purplish, O=other
Silk Color = The color of the silk when it is at least 1–2 inches long. Y = yellowish R = reddish, P = purplish, O=othe

| PEDIGREE | Br.ROOT G/R/P | TILLERS N<F<P | FEMALE QUALITY E>G>F>P | KERNEL ROWS | COB COLOR W/P/R/DR | KERNEL TYPE F/SD/D | CROWN COLOR W/LY/DY/Ot | BODY COLOR W/Y/O/Ot | % YIELD COMPARED TO "F" |
|---|---|---|---|---|---|---|---|---|---|
| F | P | N | E | 12.18 | P | D | DY | 0 | |
| 72153 | R | N | G | 16.18 | P | SD | DY | 0 | -32 |
| 72156 | R | N | E | 16.18 | P | SD | DY | 0 | 15 |
| 89101 | P | N | E | 20.24 | P | D | DY | 0 | 29 |
| 89103 | R | F | E | 16.20 | 5 W,9 P,4 | D | 11 DY, 7 | 0 | 13 |
| 89104 | P | N | E | 22.24 | P | SD | DY | 0 | 21 |
| 89109 | P | N | E | 18.22 | P | D | DY | 0 | 10 |
| 895610 | R | N | G | 16.20 | P | SD | DY | 0 | -7 |
| 895619 | R | N | G | 16.18 | P | SD | DY | 0 | -26 |
| 89569 | R | N | E | 18.20 | P | SD | DY | 0 | 10 |
| 8982 | P | N | E | 16.20 | P | D | DY | 0 | 13 |
| B 8985 | 4 P/9 R | N | E | 16.20 | P | D | DY | 0 | 26 |
| 8987 | P | N | E | 16.20 | P | SD | DY | 0 | 6 |
| 8988 | P | F | E | 18.22 | P | SD | DY | 0 | 21 |
| 8989 | P | N | E | 18.20 | P | D | DY | 0 | 29 |
| 89810 | P | N | E | 14.18 | P | SD | DY | 0 | 42 |
| 89811 | P | N | E | 18.24 | P | SD | DY | 0 | 14 |
| 89815 | R | N | E | 18.20 | P | D | DY | 0 | 6 |

Brace Root color = G = green, R = reddish, P = purplish
Tillers = N = none, F = few (<10 plants/plot with tillers)
Female Quality = General rating on seed size, seed quality, ear size, and yield. X = excellent, G = good, F = fair, P = poor.
Kernel rows = The ran e in the number of kernel rows on the ear.
Cob Color = W = white, P = pink, R = red, DR = dark red
Kernel Type = The type of kernel. F = flint, SD = shallow dent, D = dent
Crown Color = Kernel crown color. W = white, LY = light yellow, DY = dark yellow, O = orange, Ot = other.
Body Color = Kernal body color. W = white, Y = Yellow, O = orange, Ot = other
% Yield compared to F = An index used to show the % yield of a given entry, compared to BE81 and BE86.

The agronomic characteristics of the resultant plants in hybrid combination with a non-GLS improved male were tested. The results of these tests are shown in FIG. 2.

Referring to FIG. 2 all hybrids have a common parent. Hybrid Z has the selected inbred while, Hybrid A and B have inbred parents derived from the "F" inbred parent which is susceptible to Gls; herein designated "F". The desired inbreds in A & B contain the GLS resistance material derived from the previously described process. Note that the yield of hybrid A containing the present invention, was eight bushels per acre higher than hybrid Z. Hybrid B containing the present invention was ten bushels higher than the yield of hybrid Z. Likewise, the other characteristics such as moisture, stalk lodging (% SL) and root lodging (% RL) of hybrid A and hybrid B are comparable to hybrid Z. The moisture (MST) of both hybrid A and hybrid B is higher than hybrid Z. This data are based on two locations.

Thus the yield and background of the targeted inbred "F" has been carried forward into the two GLS inbreds in the improved hybrids A & B. The GLS resistance of hybrid A and hybrid B is not as high as is the resistance of the same hybrid which has GLS material in both parents, but it is still at improved levels over hybrid Z's resistance to GLS.

It would achieve the greatest GLS resistance in the resultant plant if both male and female inbreds were fixed for all four gene locations. The recessive gene action can be fixed in both parents to carry the trait into the hybrid. Additionally, fixing both of the genes having additive-dominant gene action is preferable.

This invention provides a repeatable method of obtaining GLS tolerant inbred lines having the elite characteristics and the resistance which can be employed to produce commercially acceptable GLS resistant hybrids.

This invention provides a repeatable method of obtaining GLS resistant inbred lines having the targeted elite characteristics and the GLS resistance. These inbred lines can be crossed to produce commercially acceptable GLS resistant hybrids with all four loci originating from Va14 and a genomic background of which is a mixture of the two improved elite inbreds.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. An improved maize plant, and parts thereof, which evidences a resistance response to Gray Leaf Spot (GLS) comprising a genome, homozygous with respect to genetic alleles which are native to a first parent and nonnative to a second parent of the improved maize plant, wherein said second parent evidences significantly less resistant response to GLS than said first parent and said improved plant comprises alleles from said first parent that evidences resistance to GLS in hybrid combination in at least two loci selected from: (locus 1) chromosome 1, proximate map unit 124 through 135, (locus 2) chromosome 2, proximate map unit 64 through 91, (locus 3) chromosome 5, proximate map unit 103 through 146 and (locus 4) chromosome 8, proximate map unit 129 through 136; whereto said map units correspond to the maize chromosome map of FIG. 3, said resistance not significantly less than that of the first parent in the same hybrid combination, and yield and moisture characteristics which are not significantly different than those of the second parent in the same hybrid combination.

2. The inbred maize plant of claim 1 comprising each of loci 1 through 4 and having improved resistance to GLS when compared to a substantially identical inbred maize plant not comprising said loci.

3. An inbred maize plant, and the parts thereof having a genome different from the genome of its parents exhibiting a resistance response to Gray Leaf Spot (GLS), comprising a genome which is homozygous in respect to alleles within identifiable chromosomal regions on at least two of chromosomes 1, 2, 5 and 8, which are exogenous to one of the original parent's genomes and endogenous to maize inbred Va14, or progeny thereof.

4. A maize plant having a Gray Leaf Spot (GLS) resistance genome containing genes from a maize line other than Va14 and containing genes associated with said GLS resistance from a donor parent Va14, or progeny thereof, said genes located in at least two or more of the loci selected from: (locus 1) chromosome 1, proximate map unit 124 through 135, (locus 2) chromosome 2, proximate map unit 64 through 91, (locus 3) chromosome 5, proximate map unit 103 through 146 and (locus 4) chromosome 8, proximate map unit 129 through 136: wherein said map units correspond to the maize chromosome map of FIG. 3.

5. A plant as claimed in claim 4, which is homozygous at three of the loci numbered 1 to 4 specified in claim 3.

6. A plant as claimed in claim 4, in which the donor resistant parent is a resistant hybrid comprising the corn line designated Va14.

7. An maize plant, and parts thereof, as claimed in claim 1 comprising the progeny of a cross between first and second inbred lines, alleles conferring resistance to Gray Leaf Spot (GLS) being present in the homozygous state in the genome of one or the other or both of said first and second inbred lines such that the genome of said first and second inbreds together donate to the hybrid a complement of alleles necessary to confer the resistance to GLS.

8. A method for the production of an inbred maize plant adapted for conferring, in hybrid combination with a suitable second inbred, resistance to Gray Leaf Spot (GLS) comprising:

(a) selecting a first donor parental line possessing the desired GLS resistance having at least two of the resistant loci selected from: (locus 1) chromosome 1. proximate map unit 124 through 135, (locus 2) chromosome 2, proximate map unit 64 through 91, (locus 3) chromosome 5, proximate map unit 103 through 146 and (locus 4) chromosome 8, proximate map unit 129 through 136; wherein said map units correspond to the maize chromosome map of FIG. 3, and crossing same with a second parental line which is high yielding in hybrid combination, to produce a segregating plant population:

(b) screening the plant population for identified chromosomal loci of one or more gene associated with the resistance to the GLS trait; and (c) selecting plants from said population having said identified chromosomal loci for further screening until a line is obtained which is homozygous for resistance to GLS at sufficient loci to give resistance to GLS in hybrid combination.

9. A Gray Leaf Spot resistant hybrid and parts thereof formed by crossing two maize plants according to claim 3.

10. A maize plant and parts thereof formed by selfing the Gray Leaf Spot resistant hybrid of claim 9.

11. A Gray Leaf Spot resistant hybrid and parts thereof formed with the improved maize plant according to claim 2.

12. A maize plant and parts thereof formed by selfing the Gray Leaf Spot resistant hybrid of claim 11.

* * * * *